US007598246B2

(12) United States Patent
Dixon et al.

(10) Patent No.: US 7,598,246 B2
(45) Date of Patent: *Oct. 6, 2009

(54) BISPHOSPHONATE CONJUGATES AND METHODS OF MAKING AND USING THE SAME

(75) Inventors: H.B.F. Dixon, Cambridge (GB); Marat Karpeisky, Lafayette, CO (US); Alexander Karpeisky, legal representative, Lafayette, CO (US); Nelly Padioukova, Moscow (RU); Sergey Mikhailov, Moscow (RU); Grigorii Tzeitline, Moscow (RU)

(73) Assignee: MBC Pharma, Inc., Aurora, CO (US)

( * ) Notice: Subject to any disclaimer, the term of this patent is extended or adjusted under 35 U.S.C. 154(b) by 535 days.

This patent is subject to a terminal disclaimer.

(21) Appl. No.: 10/742,453

(22) Filed: Dec. 18, 2003
(Under 37 CFR 1.47)

(65) Prior Publication Data

US 2005/0026864 A1 Feb. 3, 2005

Related U.S. Application Data

(63) Continuation-in-part of application No. 09/731,598, filed on Dec. 7, 2000, now Pat. No. 6,750,340, which is a continuation-in-part of application No. 09/283,440, filed on Apr. 1, 1999, now Pat. No. 6,214,812.

(60) Provisional application No. 60/080,500, filed on Apr. 2, 1998.

(51) Int. Cl.
*A61K 31/53* (2006.01)
*C07D 251/10* (2006.01)
(52) U.S. Cl. ...................... 514/241; 544/180
(58) Field of Classification Search ................. 544/180, 544/195; 514/241
See application file for complete search history.

(56) References Cited

U.S. PATENT DOCUMENTS

| | | | | |
|---|---|---|---|---|
| 4,621,077 A | | 11/1986 | Rosini | 514/108 |
| 5,130,304 A | | 7/1992 | Binderup | 514/91 |
| 5,358,941 A | | 10/1994 | Bechard | 514/102 |
| 5,428,181 A | * | 6/1995 | Sugioka et al. | 552/506 |
| 5,488,041 A | | 1/1996 | Barbier | 514/108 |
| 5,580,571 A | | 12/1996 | Hostetler | 424/443 |
| 5,721,219 A | | 2/1998 | Ingall | 514/47 |
| 5,760,013 A | * | 6/1998 | Hwu et al. | 514/49 |
| 5,900,410 A | * | 5/1999 | Hartmann | 514/81 |
| 6,121,253 A | | 9/2000 | Han et al. | 514/102 |
| 6,140,518 A | | 10/2000 | Gallagher et al. | 552/506 |
| 6,605,603 B1 | | 8/2003 | Roldan et al. | 514/103 |
| 6,750,340 B2 | * | 6/2004 | Padioukova et al. | 544/243 |

FOREIGN PATENT DOCUMENTS

| WO | WO 88/00829 | 2/1988 |
|---|---|---|
| WO | WO 91/10646 | 7/1991 |
| WO | WO 95/35704 | 8/1998 |

OTHER PUBLICATIONS

Gough, GR et al, Three new adenosine triphosphate analogs. Synthesis and effects on isolated gut, CA 80: 10270 (1974).*
Gough et al., J. Me. Chem. (1973) vol. 16(10), pp. 1188-1190.*
Buxton et al., Ciprofloxacin conjugated to bisphosphonate: Characterization of bone affinity in vitro, *Abstracts of the Interscience Conference on Antimicrobial Agents and Chemotherapy*, San Diego, California, 1998, vol. 38, p. 29, XP008043693.
Murud et al, Influence of pretreatment with 3-amino-1-hydroxypropylidene-1, 1-bisphosphonate (APB) on organ uptake of 211At and 125I-labeled amidobisphosphonates in mice, *Nuclear Medicine and Biology* 1999, vol. 26, No. 7, pp. 791-794, XP002319673.
Shtil et al., Novel bisphosphonate -based compounds for circumventing drug resistance in the bone-targeting human tumor cells, *Proceedings of the American Association for Cancer Research Annual Meeting*, San Francisco, California, 2000, No. 41, p. 398, XP002319674.
Buxton et al., Novel local drug delivery of antibiotic-bisphosphonate: binding and antibacterial effects, *FASEB J.* 2001, vol. 15, No. 4, p. A587, XP008043697.
Fujisaki et al., Osteotropic drug delivery system (ODDS) based on bisphosphonic prodrug, *Proceedings of the International Symposium f Controlled Release of Bioactive Materials* 22nd, 1995, abstract, figure 1, XP008043630.
Fleisch (Feb. 1998) Endocrine Reviews 19(1): 80-100, Biophosphonates: Mechanisms of Action.
Hosain et al. (Jan. 1996) The Journal of Nuclear Medicine 37(1):105-107, Targeted delivery of antineoplastic agent to bone: biostribution studies of technetium-99m-labeled gembisphosphonate conjugate of methotrexate.
Klein et al. (1998) Journal of Cellular Biochemistry 68:86-194, Structurally Different Biophosphonates Exert Opposing Effects of Alkaline Phosphatase and Mineralization in Marrow Osteoprogenitors.
Reinholtz et al. (Feb. 2002) Breast Cancer Research and Treatment, 71(3):257-268, Distinct mechanisms of biophosphonate action between osteoblasts and breast cancer cells: identity of a potent new biophosphonate analogue.
Rogers et al. (1995) Molecular Pharmacology 47:398-402, Structure-Activity Relationships of New Heterocycle-Containing Biophosphonates as Inhibitors of Bone Resorption and as Inhibitors of Growth of *Dictyostelium discoideum* Amoebae.
Hershey and Monro (1966) "A Competitive Inhibitor of the GTP Reaction in Protein Synthesis" J. Mol. Biol. 18:68-76.
Padyukova et al. (1999) "Synthesis and Properties of Novel NTP Derivatives" Nucleosides & Nucleotides 18(4&5):1013-1014.

* cited by examiner

*Primary Examiner*—Taofiq A Solola
(74) *Attorney, Agent, or Firm*—Swanson & Bratschun, L.L.C.

(57) ABSTRACT

The present invention provides novel bisphosphonate conjugates, pharmaceutical compositions comprising bisphosphonate conjugates and methods of using such analogs in the treatment of bone cancer, bone-related diseases and diseases of the soft tissues surrounding bones.

13 Claims, 3 Drawing Sheets

Reagents & Conditions: i) EtOH/water; ii) NaBH$_4$/EtOH/water a: R=H
b: R=PO$_3$H$_2$

BISPHOSPHONATE CONJUGATES AND METHODS OF MAKING AND USING THE SAME

CROSS-REFERENCE TO RELATED APPLICATIONS

This application is a continuation-in-part of U.S. patent application Ser. No. 09/731,598 filed 7 Dec. 2000 now U.S. Pat. No. 6,750,340 which is a continuation-in-part application of U.S. patent application Ser. No. 09/283,440 filed on 1 Apr. 1999 now U.S. Pat. No. 6,214,812 which claims priority to U.S. Provisional Patent Application No. 60/080,500 filed 2 Apr. 1998. The disclosures of these applications are incorporated herein by this reference.

FIELD OF THE INVENTION

The present invention is directed to bisphosphonate compounds, and in particular, bisphosphonate conjugates that are useful in the treatment of soft tissues surrounding bone and bone-related diseases, such as bone cancer and osteoporosis.

BACKGROUND OF THE INVENTION

Bone degeneration diseases, including Paget's Disease and osteoporosis have proven difficult to treat because the mechanisms involved in the development and progression of these diseases are not well understood. Bisphosphonates are synthetic analogs of pyrophosphates characterized by a phosphorus-carbon-phosphorus backbone that renders them resistant to hydrolysis and are known to be useful in the treatment of these degenerative bone disorders. The chemical properties of the bisphosphonates vary based on different substitutions at the carbon atom of the phosphorus-carbon-phosphorus backbone.

Bisphosphonates bind strongly to hydroxyapatite on the bone surface and act to reduce and inhibit the activity of osteoclasts; cells functioning in the absorption and removal of osseous tissue. The anti-resorptive effect of bisphosphonates is also mediated through effects on osteoblasts; cells that function in the production of bone. Thus, biophosphonates are used clinically to inhibit bone resorption in disease states such as Paget's disease, osteoporosis, metastatic bone diseases, and malignant and nonmalignant hypercalcemia. Bisphosphonates are also used to mediate anti-cancer effects by modifying the bone surface, altering the bone microenvironment, inhibiting specific enzymatic pathways and inducing apoptosis in osteoclast and tumor cells.

Bisphosphonates that are currently used therapeutically include alendronate, clodronate, etidronate, pamidronate, tiludronate, ibandronate, zoledronate, olpadronate, residronate and neridronate. Additionally, bone scanning agents based on the use of bisphosphonic acid compounds have been used in the past to produce high definition bone scans (see e.g., U.S. Pat. No. 4,810,486 to Kelly et. al). Bisphosphonate derivatives have been used as therapeutic agents for bone diseases such as osteoporosis, rheumatoid arthritis, and osteoarthritis (see e.g., U.S. Pat. No. 5,428,181 to Sugioka et. al). In the past, however, bisphosphonate therapies have frequently been accompanied by severe side effects such as retardation of bone development and somatic growth.

Therefore, a need exists for novel bisphosphonate compounds that act as delivery vehicles to target and deliver therapeutic agents to bone and the surrounding soft tissue, allowing selective treatment of these tissues while eliminating or minimizing the severe side effects previously seen with bisphosphonate therapies.

SUMMARY OF THE INVENTION

One embodiment of the present invention provides bone-seeking conjugates containing anticancer or antibiotic compounds or derivatives thereof linked to bisphosphonates. When linked to a moiety having antineoplastic or antibiotic properties, bisphosphonates act as vehicles for the targeted delivery of these therapeutic entities to bone. The chemical bond(s) connecting the bisphosphonate and the drug is/are stable enough to survive in the bloodstream and yet is/are cleaved to liberate the drug when the conjugate binds to bone.

Because these conjugates are capable of releasing antibacterial and cytotoxic components upon binding with bone tissue, they are useful in the treatment and prevention of bone cancer, bone infections and disorders in soft tissues surrounding bone. For example, in the case of osteomyelitis, certain therapeutic antibiotics can be coupled to the bisphosphonate carrier molecule for delivery of high concentrations of antibiotic to various sites of bone infection. Examples of useful antibiotics that can be conjugated with the bisphosphonates of the present invention include fluoroquinolones, penicillin antibiotics, aminoglycosides and cephalosporins. Examples of useful anticancer derivatives that can be conjugated with the bisphosphonates of the present invention include 5-fluorouracil, cytarabine, cisplatin, doxorubicin, epirubucin, streptozocin and methotrexate.

One embodiment of the present invention provides novel bisphosphonate conjugates that are capable of delivering antibacterial and/or anti-neoplastic (cytotoxic) residues to the bone and surrounding tissues. Such conjugates will release their therapeutic component upon binding to the bone tissue and thus are useful in the treatment and prevention of bone primary tumors, metastases of non-bone tumors to bones and infections of bone and surrounding soft tissue.

The conjugates of the present invention comprise esters, thioesters or amides of substituted bisphosphonates, and anhydrides formed between a substituted bisphosphonate and a phosphate, thiophosphate or phosphoramidate, which are analogs of triphosphates. The labile phosphoanhydride bond in such analogs provides release of the therapeutic compound upon binding with the bone or surrounding tissues.

Another embodiment of the present invention provides bisphosphonate conjugates linked to therapeutic entities that are effective in treating or modulating cancers or infections of bone and bone-surrounding tissues such as amino acids, nucleic acids, protein toxins, protein and/or peptide growth factors and hormones that promote bone growth and bone marrow proliferation.

Another aspect of the present invention provides bisphosphonate conjugates that offer a delivery vehicle with which to deliver and concentrate drugs and proteins to normal and abnormal bone tissue and soft tissue surrounding bones. These abnormalities are generally referred to as bony lesions. As used herein, bony lesions include, but are not limited to, bone cancer, osteomyelitis, soft tissue infections surrounding bone, bone marrow abnormalities, and bone diseases such as Paget's disease.

The present invention thus provides novel bisphosphonate conjugates, pharmaceutical compositions comprising bisphosphonate conjugates and methods of using such analogs in the treatment of bone cancer, bone-related diseases and diseases of the soft tissues surrounding bones.

DETAILED DESCRIPTION OF THE INVENTION

Figure 1:
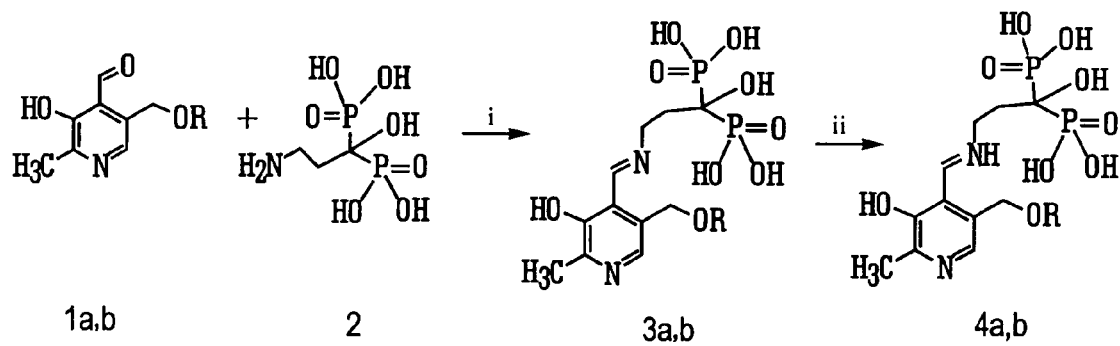
FIG. 1 is the scheme for the synthesis of vitamin $B_6$-bisphosphonate conjugates.

The present invention relates to novel bisphosphonate conjugates that are capable of delivering therapeutic compounds such as antibacterial and/or anti-neoplastic (cytotoxic) compounds or peptide or protein compounds having growth stimulating properties to bone and soft tissues surrounding bone. The conjugates release the therapeutic components upon binding to the bone tissue and are therefore useful in the treatment and prevention of primary bone tumors, metastases to bone tissues, bone inflammation, bone infections and disorders of the growth of bone and bone marrow.

Bisphosphonates are synthetic compounds containing two phosphonate groups bound to a central (geminal) carbon (the P—C—P backbone) that are used to prevent bone resorption in a number of metabolic and tumor-induced bone diseases including multiple myeloma. Bisphosphonate treatment is associated with an increase in patient survival, indicating that these compounds have a direct effect on the tumor cells.

Bisphosphonates may contain two additional chains bound to the central geminal carbon. The presence of these two side chains allows numerous substitutions to the bisphosphonate backbone and therefore the development of a variety of analogs with different pharmacological properties. The activity varies greatly from compound to compound, the newest bisphosphonates being 5,000 to 10,000 times more active than etidronate, the first bisphosphonate described. The mechanism of action of bisphosphonates includes a direct effect exerted on osteoclast activity, direct and indirect effects on osteoclast recruitment mediated by cells of the osteoblastic lineage and involving the production of an inhibitor of osteoclastic recruitment and a shortening of osteoclast survival by apoptosis.

High doses of bisphosphonates can also inhibit mineralization through a physicochemical inhibition of crystal growth. One substituent on the geminal carbon together with the P—C—P backbone are primarily responsible for binding to bone mineral and for the physicochemical actions of the bisphosphonates. These interactions are optimized by the presence of a hydroxyl group as at least one substituent on the geminal carbon. The remaining substituent on the geminal carbon is responsible for the anti-resorptive action of the bisphosphonates and small modifications or conformational restrictions at this part of the molecule result in marked differences in anti-resorptive potency. The presence of a nitrogen functionality in an alkyl chain or in a ring structure in one of the substituents on the geminal carbon greatly enhances the anti-resorptive potency and specificity of bisphosphonates for bone resorption and most of the newer potent bisphosphonates contain a nitrogen in their structure.

The biological effects of bisphosphonates in calcium-related disorders are attributed to the incorporation of the bisphosphonates into bone, enabling direct interaction with osteoclasts and/or osteoblasts. The high accumulation of bisphosphonates in bone, due to their high affinity for hydroxyapatite, is essential for mediating both the in vitro and in vivo activity. Nitrogen-containing bisphosphonates are known to act by binding to a specific intracellular target at a site complementary in structure to the bisphosphonate side chain.

Recent evidence suggests that the whole bisphosphonate molecule is essential for anti-resorptive action. Thus, although the basic structural requirements for bisphosphonate actions have been defined, precise structure-activity relationships for the bisphosphonate side chains indicate that at least the newer generations of nitrogen-containing bisphosphonates act by binding to a specific target at a site that is complementary in structure to the bisphosphonate side chain.

The bisphosphonate conjugates of the present invention have the chemical structure:

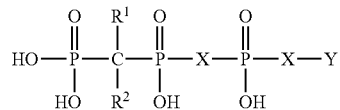

wherein, each X is independently O, S or NH,

Y is an anti-cancer or antibiotic compound or derivative thereof, $R^1$ and $R^2$ are independently H, Z, OZ, NZ, SZ; and, Z is H, alkyl, cycloalkyl, aryl, heteroaryl or $NH_2$.

As used herein, an "alkyl" group refers to a saturated aliphatic hydrocarbon, including straight-chain and branched-chain alkyl groups. Preferably, the alkyl group has 1 to 12 carbons. More preferably it is a lower alkyl having from 1 to 7 carbons, and more preferably 1 to 4 carbons. The alkyl group may be substituted or unsubstituted. When substituted, the substituent group(s) may include hydroxy, cyano, alkoxy, $NO_2$ or $N(CH_3)_2$, amino, or SH.

As used herein, a "cycloalkyl" group refers to a cyclic alkyl group having from three to ten, and preferably five or six carbon atoms forming the alkyl ring.

As used herein, an "aryl" group refers to an aromatic group which has at least one ring having a conjugated pi electron system and includes carbocyclic aryl, heterocyclic aryl and biaryl groups; all of which may be optionally substituted. Substituent(s) on these groups may include halogen, trihalomethyl, hydroxyl, SH, cyano, alkoxy, alkyl, alkenyl, alkynyl, and amino groups.

As used herein, "heteroaryl" refers to an aromatic ring having from 1 to 3 heteroatoms in the aromatic ring with the remainder of the atoms in the ring being carbon atoms. Suitable heteroatoms include oxygen, sulfur, and nitrogen, and exemplary heteraryls include furanyl, thienyl, pyridyl, pyrrolyl, pyrrolo, pyrimidyl, pyrazinyl and imidazolyl. These heteroaryl rings may also be substituted. Substituents on these heteroaryl groups may include halogen, trihalomethyl, hydroxyl, SH, cyano, alkoxy, alkyl, alkenyl, alkynyl, and amino groups.

As used herein, a "catalytic nucleic acid" is a nucleic acid molecule capable of catalyzing reactions including, but not limited to, site-specific cleavage and/or ligation of other nucleic acid molecules, cleavage of peptide and amide bonds, and trans-splicing. The enzymatic nucleic acid is able to intramolecularly or intermolecularly cleave RNA or DNA and thereby inactivate a target RNA or DNA molecule.

As used herein, the term "enzymatic nucleic acid" is used interchangeably with phrases such as ribozymes, catalytic RNA, enzymatic RNA, catalytic DNA, nucleozyme, DNAzyme, RNA enzyme, endoribonuclease, minizyme, leadzyme or DNA enzyme. All of these terms describe nucleic acid molecules having enzymatic activity.

As used herein, "antisense nucleic acid" is a non-enzymatic nucleic acid molecule that binds to target RNA by means of RNA-RNA or RNA-DNA or RNA-PNA (protein nucleic acid) interactions and alters the activity of the target RNA.

As used herein, "anti-cancer compound" refers to any compound having anti-cancer activity.

As used herein, an "unmodified nucleic base" or "natural nucleic base" is any base found in a nucleic acid including adenine, cytosine, guanine, uracil, and thymine having no additional substituents or modifications.

As used herein, a "modified nucleic base" is any base found in a nucleic acid which contains a modification in the chemical structure of an unmodified nucleic base.

As used herein, an "unmodified sugar" is beta-D-ribofuranose, or 2-deoxy-beta-D-ribofuranose.

As used herein, a "modified sugar" is any sugar moiety containing a modification in the chemical structure of an unmodified sugar.

The bisphosphonate conjugates of the present invention contain both an osteotropic moiety and a therapeutic moiety that is released from the osteotropic moiety upon binding of the conjugates to bone tissue. The covalent bond(s) connecting the bisphosphonate moiety and the therapeutic component are stable enough to survive in the bloodstream but are cleaved to liberate the drug when the conjugate binds to bone tissue, releasing the therapeutic component to the bone or to soft tissue surrounding the bone.

These bisphosphonate conjugates comprise conjugates formed between a substituted bisphosphonate and a substituted phosphoric, thiophosphoric or amidophosphoric acid. Thus, these conjugates are analogs of triphosphates. It is the labile phosphoanhydride bonds in these analogs that release the conjugated therapeutic compounds upon binding with the bone. In this way, the bisphosphonate conjugates of the present invention can be used to target covalently bound therapeutic compounds to bone and soft tissue surrounding bone.

One embodiment of the present invention includes anti-cancer drugs that are coupled to bisphosphonate or derivatives of bisphosphonate substituted at the geminal carbon. The anti-cancer drugs may include, but are not limited to, nucleosides and/or acyclo-nucleosides in which the sugar or nucleic base is modified or unmodified (natural), antisense and catalytic oligonucleotides, amino acids, peptides, polypeptides or proteins having cytostatic or antineoplastic properties. The bisphosphonate may also be conjugated to combinations of one or more of these anti-cancer compounds. Exemplary anticancer compounds for conjugation to the bisphosphonate moiety include, but are not limited to, cytarabine, cisplatin, doxorubicin, epirubucin, streptozocin and methotrexate. Additionally, the bisphosphonate or bisphosphonate derivatives may be conjugated to nucleosides or nucleoside-like compounds having cytostatic or neoplastic activity. Exemplary nucleoside or nucleoside-like compounds that can be conjugated to the bisphosphonate compounds of the present invention include compounds having the structure:

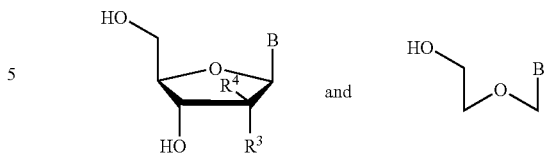

wherein $R^3$ and $R^4$ are independently H, OH or F and B is a natural or modified nucleic base or derivative thereof. Exemplary modified nucleic bases include compounds having the structure:

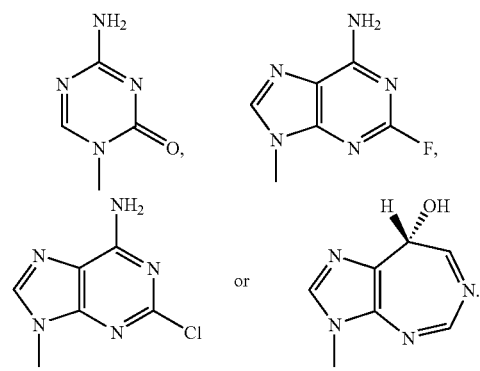

These nucleoside or nucleoside-like compounds can be linked to the bisphosphonate or bisphosphonate derivatives through a linker group. Exemplary linking moieties include phosphate or thiophosphate groups. These bisphosphonate conjugates are useful in the treatment of primary bone tumors, bone metastases (i.e. metastases to bone tissues from malignant tissue elsewhere in the body), bone inflammation, bone infections and disorders of the growth of bone and bone marrow. Thus, the present invention includes methods of treating a mammal in need of anti-cancer therapy with compounds of the present invention having an anti-cancer compound coupled to a bisphosphonate in a therapeutically effective amount sufficient to impart a chemotherapeutic response in the mammal.

Another embodiment of the present invention includes a bisphosphonate or derivatives of bisphosphonate substituted at the geminal carbon coupled to a compound having bacteriostatic or antibiotic activity. These conjugates have been found to be particularly useful in the treatment of infections or inflammation of the bone tissue or of soft tissues surrounding bone. In this embodiment, therapeutic antibiotics can be coupled to the bisphosphonate carrier molecule for delivery of high concentrations of antibiotics to the sites of bone or soft tissue infection. The covalent bond(s) connecting the bisphosphonate moiety and the antibiotics are cleaved to liberate the drug when the conjugate binds to bone tissue, releasing the antibiotic to the bone or to soft tissue surrounding the bone. Examples of antibiotics which can be conjugated to the bisphosphonate carriers include, but are not limited to, fluoroquinolones such as ciprofloxacin, penicillin antibiotics such as ampicillin, aminoglycoside antibiotics such as gentamycin and cephalosporin antibiotics such as cephalexin. Therefore, the present invention includes methods of treating a mammal in need of antibiotic or anti-inflammatory therapy with compounds of the present invention having an antibiotic or anti-inflammatory compound coupled to a bisphosphonate in a therapeutically effective amount to impart antibiotic or anti-inflammatory responses in the mammal.

Another embodiment of the present invention is a bisphosphonate or derivatives of bisphosphonate substituted at the geminal carbon moiety conjugated to a protein or peptide growth factor or hormone that promotes bone growth and/or bone marrow proliferation. These conjugates are useful in the treatment of diseases or abnormalities of bone formation, bone resorption or bone growth. Thus, the present invention includes methods of treating a mammal in need of therapy to slow, stabilize or increase bone growth with compounds of the present invention having bone growth regulating proteins coupled to a bisphosphonate in a therapeutically effective amount to impart the desired negative or positive bone growth response in the mammal.

Another embodiment of the present invention is directed to novel vitamin $B_6$-bisphosphonate conjugates for use in the treatment and diagnosis of bone diseases. Vitamin $B_6$ and its phosphorylated derivatives are also known to have a high affinity to proteins and to enhance transport of small molecular weight compounds through cell membranes. Thus novel $B_6$-bisphosphonate conjugates of the present invention are well suited for the treatment of disorders relating to the metabolism of calcium and of other, especially bivalent, metals. They may be used both for the treatment of diseases in the skeletal system, especially of bone formation and resorption disorders, such as osteoporosis and Paget's disease, as well as for the treatment of diseases in the soft tissues, such as deposition and mineralization disorders and bone formation.

Preferred vitamin $B_6$-bisphosphonate conjugates include, but are not limited to: 3-(N-pyridoxylamino)-I-hydroxy-propyliden-1,1-bisphosphonic acid, and 3-(N-[5'-phospho]-pyridoxyl amino)-1-hydroxy-propyliden-1,1-bisphosphonic acid.

Preferably, the $B_6$-conjugates used in the present invention contain at least one pyridoxamine residue. Representative compounds include the following:

(i)  3-(N-[5'-phospho]-pyridoxylamino)¥1-hydroxypropyliden-1,1-bisphosphonic acid;
(ii) 3-(N-pyridoxylamino)-1-hydroxypropyliden-1,1-bisphosphonic acid;
(iii) 1-(N-[5'-phospho]-pyridoxylamino)-methylen-1,1-bisphosphonic acid;
(iv) 1-(N-pyridoxyl amino)-methylen-1,1-bisphosphonic acid;

The preferred complexing agent of the invention is 3-(N-pyridoxylamino)-1-hydroxy-propyliden-1,1-bisphosphonic acid, which shows high and rapid uptake in bone without any apparent concomitant disadvantages. 3-(N-pyridoxylamino)-1-hydroxypropyliden-1,1-bisphosphonic acid, is believed to be a new compound and, accordingly, this compound and its derivatives (e.g., its various salts, including sodium salts) forms a further aspect of the invention. This compound, as its sodium salt, may be prepared according to the reaction scheme shown in FIG. 1.

The active compounds are effective over a wide dosage range and are generally administered in a pharmaceutically effective amount. It will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

Synthesis of Bisphosphonate Conjugates

Referring to FIG. 1, the conjugates of the present invention may be prepared by mixing an aqueous solution of the conjugate complexant, or a non-toxic salt thereof, with a solution of the reducing agent. The pH of the mixture may, if desired, be adjusted within the range of from about 3 to about 9, preferably between about 4 to about 8. If desired, the mixture may be dispersed into sealed vials, freeze dried and, if not already sterile, finally sterilized.

Novel bisphosphonate conjugates, i.e., molecules containing the phosphorus-oxygen-phosphorus-carbon-phosphorus backbone, are structurally similar to derivatives and analogs of nucleoside-5'-triphosphates. For this reason, known methods for synthesis of nucleoside-5'-triphosphates were tested to find effective experimental protocols for synthesis and purification of novel bisphosphonate conjugates. A variety of chemical methods for the preparation of nucleoside-5'-triphosphates from nucleoside monophosphates are known. Referring to FIG. 1, the nucleoside monophosphates were activated as imidazolides using the 1,1'-carbonyldiimidazole method because the reaction of mononucleotides with 1,1'-carbonyldiimidazole (CDI) occurs under relatively mild conditions compared with other methods and does not require a purification step. For example, reaction of tri-n-butylammonium salt of 5'-IMP with DCI, followed by addition of tri-n-butylammonium salt of diphosphonic acid in dry DMF, gave corresponding triphosphate (I) in a high yield (74%). Triphosphates (II-III) are obtained in the same manner starting from nucleoside 5'-monophosphates. The separation of products were achieved by column chromatography on DEAE-cellulose in $HCO_3^-$ form using a concentration gradient of ammonium bicarbonate solution. The yields are summarized in the Examples provided below. The structures of prepared derivatives were proved by $^1H$ and $^{31}P$ NMR spectra and are detailed in the Examples below. $^1H$ NMR spectra of triphosphates I-III are nearly the same as those for corresponding analogs of nucleoside 5'-monophosphates. The chemical shifts of phosphorus signals in $^{31}P$ NMR spectra of the obtained derivatives I-III are similar to those published for pCH$_2$ppA.

Analogous condensation of nucleoside imidazolides with 1-hydroxyethyliden-1,1-bisphosphonic acid gave the corresponding triphosphates in poor yield due to the instability of the modified triphosphate residue during product isolation. Much better yields were obtained when the product separation was carried out under slightly acidic conditions, using column chromatography on DEAE-cellulose in the $CH_3COO^-$ form in a gradient concentration of lithium acetate (pH 4.6). It is known that the reaction of nucleoside 5'-monophosphates with DCI gave 2',3'-O-cyclic carbonates, which were very sensitive to alkaline treatment.

For the preparation of analogs (compounds VI, VII and IX in FIG. 2) the corresponding 2',3'-O-cyclic carbonates were obtained in good yield.

Figure 2:
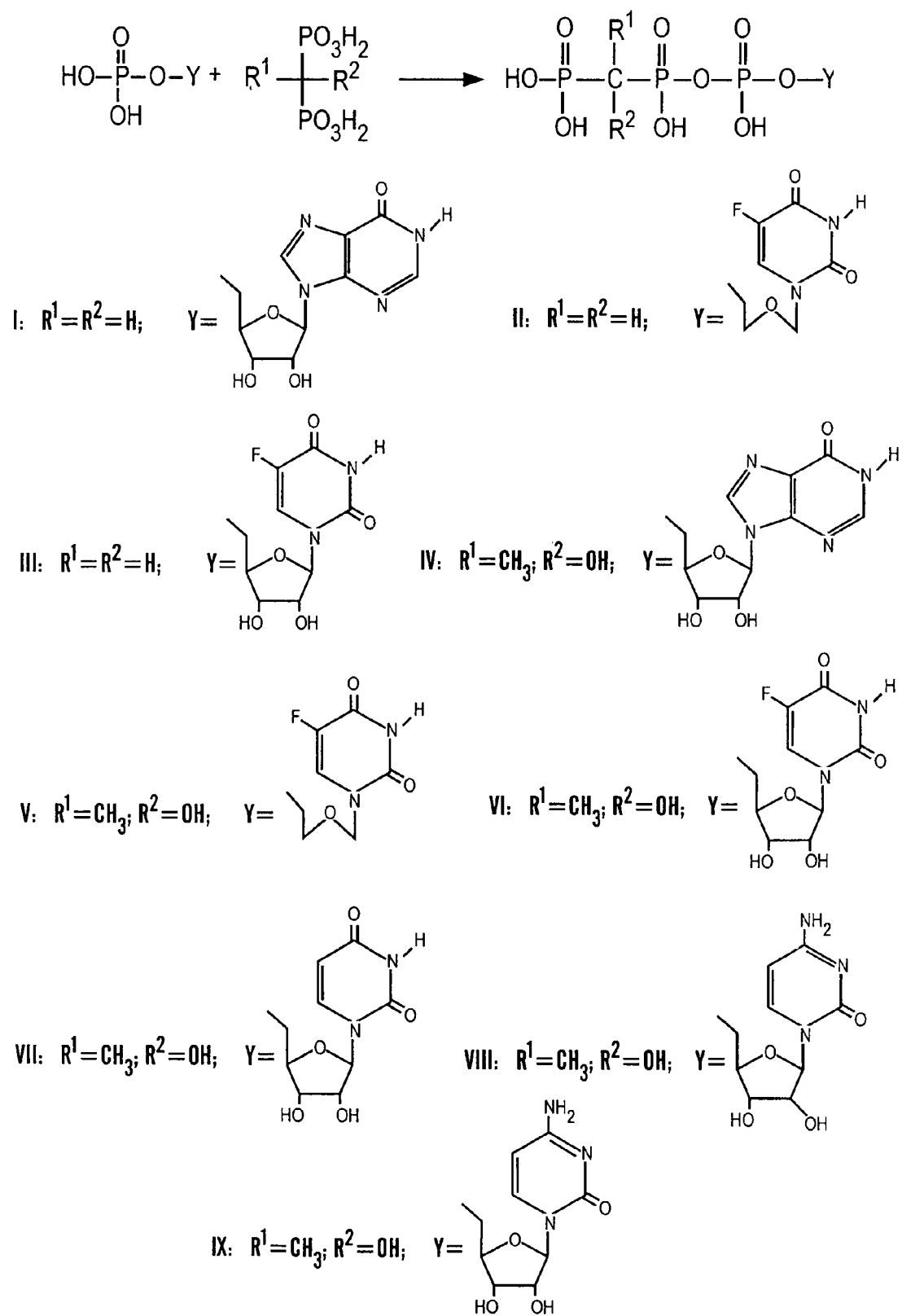
FIG. 2 is the scheme for the preparation of nucleoside-5'-triphosphate analogs.
Figure 4:
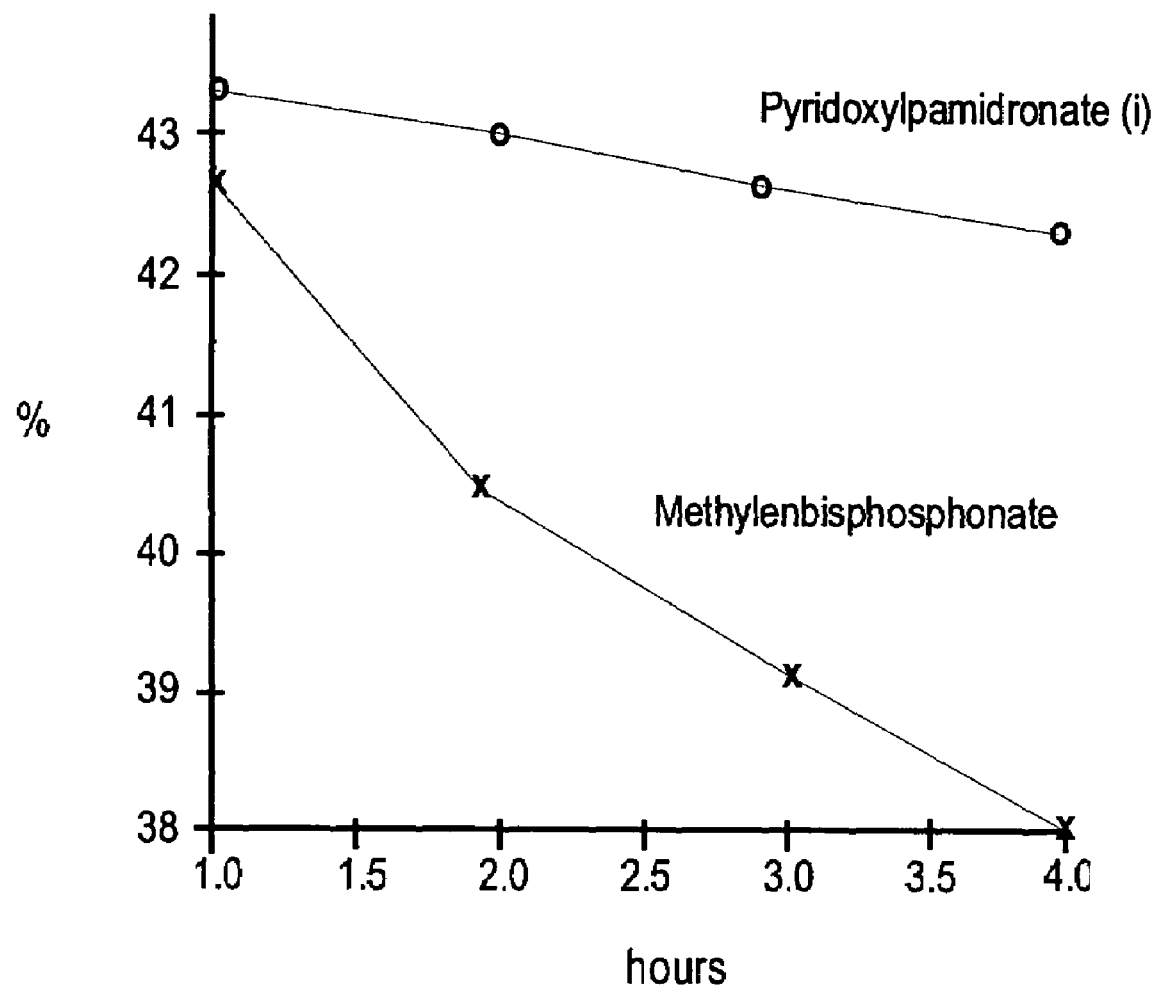
FIG. 4 shows the accumulation of radioactivity at a rat skeleton following treatment with a radioactive bisphosphonate conjugate.

Referring to FIG. 2, mild treatment with 0.5% aqueous triethylamine at room temperature for 0.5 hours was used. Due to the lower solubility of cytosine derivatives in dry DMF we have used tri-n-octylammonium salts of nucleotide-5'-phosphates in the preparation of compounds VIII and IX. A purity of derivatives thus obtained was checked by HPLC and their structures were confirmed by $^1H$ and $^{31}P$ NMR spectra. In the $^1H$-NMR spectra of compounds IV-IX, the signal of the methyl group in the P—C—Me—P backbone appears around 1.5 ppm as a triplet. Three signals of phosphorus were found in $^{31}P$ NMR spectra. Chemical shifts and the observed coupling constants $Jp_\alpha p_\beta$; J=30-33 Hz and $Jp_\gamma p_\beta$=33-39 Hz were in agreement with proposed structure. The location of β and γ phosphorus chemical shifts strongly depends upon pH. This phenomenon may be used for simplification of $^{31}$P NMR spectra when β and γ phosphorus chemical shifts having nearly the same values occur.

The present invention also encompasses the pharmaceutically-acceptable non-toxic acid addition salts of the compounds of the present invention and pharmaceutically acceptable formulations containing them. Such salts include those derived from organic and inorganic acids such as, without limitation, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

The pharmaceutical compositions of the present invention are preferably formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient or excipients. The compositions can be formulated so as to provide sustained or delayed release of active ingredient after administration to the patient by employing procedures well known in the art.

Pharmaceutical compositions of the present invention comprise one or more bisphosphonate conjugates of the present invention associated with at least one pharmaceutically-acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

In preparing a pharmaceutical formulation of the present invention, it may be necessary to mill the active compound to provide the appropriate particle size prior to combining with the other ingredients. If the active compound is substantially insoluble, it is ordinarily milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

Additional objects, advantages, and novel features of this invention will become apparent to those skilled in the art upon examination of the following examples thereof, which are not intended to be limiting.

EXAMPLES

Example 1

Synthesis of 3-amino-1-hydroxypropyliden-1,1-bisphosphonic acid

To a mixture of 12.3 g (0.15 mol) phosphorous acid, 8.9 g (0.1 mol) beta-aminopropionic acid and 50 ml chlorobenzene 33.0 g (0.24 mol) PCl$_3$ was added dropwise under stirring at 100° C. The two-layer mixture was heated at 105-110° C. for 2 h Under those conditions the bottom layer became thick and finally became solid. The reaction mixture was cooled down to 60-65° C. At this temperature 20 ml of water was added drop by drop. The layers were stirred for 15 min., cooled down to room temperature and then separated. The bottom aqueous layer was filtered through paper filter. 100 ml of isopropanol was added to the solution dropwise (60-65° C.) under stirring. The warm solution was filtered and 100 ml of ethanol was added. After 12 hours at room temperature, a precipitate was filtered off generating a yield of 12.7 g (62%) m.p. 232-234° C. To obtain a homogeneous product the solid material was boiled with 50 ml of water and insoluble substance was filtered off. Yield 10.8 g (53%), m.p. 234-236° C.

Example 2

Synthesis of 3-(N-pyridoxylamino)-1-hydroxypropyliden-1,1-bisphosphonic acid

To the solution of 189 mg (1 mmol) 3-amino-1-hydroxypropylidene-1,1-bisphosphonic acid in water (1 ml), triethylamine (0.9 ml) and ethanol (9 ml), pyridoxal hydrochloride (408 mg, 2 mmol) was added. The reaction mixture was stirred 1 h at room temperature. Then the pH of a solution was adjusted to 3 with 6 N HCl. Ethanol was evaporated and the pH of the solution was adjusted to 7 with $NH_4OH$. The solution was applied to a Dowex-50(H+) column (20 ml). The column was washed with water and the product was eluted with 2.5% $NH_4OH$. The solution was evaporated to a small volume, the residue was dissolved in water (100 ml) and applied to a DEAE-cellulose column ($HCO_3$ form). The column was washed with water (200 ml) and then eluted with the use of a linear gradient $NH_4HCO_3$ (0.05-0.3 M). The peak eluate was evaporated and the residue coevaporated with water (5×10 ml). Lyophilisation of the aqueous solution afforded the product as an ammonium salt. Yield 100 mg. 24%. $R_f$ 0.07 (B); $R_f$ 0.21 (C); $R_f$ 0.2 (D); $R_f$ 0.48 (F); $R_f$ 0.07 (E).

$^1$H NMR ($D_2O$) δ: 7.55 br s (1H, 6-OH); 4.3 s (2H, 5-$CH_2$); 2.4 s (3H, 2-$CH_3$); 2.3 m (2H, $CH_2$)

Example 3

Synthesis of 3-(N-[5'-phospho]pyridoxylamino)-1-hydroxypropyliden-1,1-bisphosphonic acid 3-Amino-1-hydroxypropylidene-1,1-bisphosphonic acid (940 mg, 4 mmol) was added to the solution of pyridoxal hydrochloride (1.632 g, 8 mmol) in ethanol (40 ml), triethylamine (4 ml), water (4 ml). The reaction mixture was stirred 3 h at room temperature. $NaBH_4$ (300 mg, 8 mmol) was added to the solution and reaction mixture was stirred 1 h at room temperature. The crystalline material was filtered off, washed with ethanol and ether. The product obtained was dissolved in 20 ml water and applied to a Dow-50 ($H^+$) column (30 ml). The column was washed with water and the product was eluted with 2.5% aqueous $NH_4OH$. The solution was evaporated to small volume. Lyophilisation of the water solution afforded product as ammonium salt, yield 875 mg, 52.5%. $R_f$ 0.07 (B); $R_f$ 0.21 (C); $R_f$ 0.2 (D); $R_f$ 0.48 (F); $R_f$ 0.07 (E)

$^1$H NMR ($D_2O$) δ: 7.38, s (1H, 6-H); 4.13 (2H, 5-$CH_2$); 3.18 t (2H, 4-$CH_2$); 2.23 s (3H, 2-$CH_3$); 2.08 m (2H $CH_2$).

$^{31}$P-NMR ($D_2O$) δ: 17.6 s

Example 4

Synthesis of Vitamin $B_6$ Conjugates with aminomethylenbisphosphonate

A. Synthesis of 1-(pyridoxylamino)-methylen-1,1-bisphosphonic acid 45 mg (0.2 mmol) of ammonium salt of aminomethylenediphosphonic acid was added to a solution of 81.6 mg (0.4 mmol) of pyridoxal-HCl in 2 ml of ethanol mixed with 0.2 ml of triethylamine and 1 ml of $H_2O$. The solution was stirred at room temperature for three hours. Then 20 mg (0.5 mmol) of $NaBH_4$ was added and the reaction mixture was again stirred for three hours at room temperature. Ethanol was evaporated in vacuum, the aqueous solution was loaded on a column with Dowex-50 ($H^+$), the column was washed with water and then the product was eluted. To the aqueous solution of the corresponding acid the aqueous ammonia solution was added, then the mixture was evaporated in a vacuum to the small volume and loaded on the column with Dowex-50 ($Na^+$), the column was washed with water and Na-salt of the product was eluted and lyophilized. The yield was 62 mg, 80%.

HPLC: Nucleosil C 18 (4×250 mm); gradient 0-5 min 0% MeCN; 5-25 min 0-80% MeCN. Purity 98%; RT approximately 12 min.

TLC: $R_f$ 0.34 on PEI-cellulose in 0.5M $NH_4HCO_3$; $R_f$ 0.4 on silufol UV 254 in isopropanol-ammonium-$H_2O$ (3:1:2); $R_f$ 0.64 on silufol in the system isopropanol-dioxan-ammonium-$H_2O$ (2:2:1:7).

$^1$H-NMR ($D_2O$): 7.6 s (1H, 6-H); 4.7 s (2H, 4'-$CH_2$); 4.6 s (2H, 5'-$CH_2$); 3.2 dd (1H, $J_{HP}$=16.24; N—CH); 2.45 s (3H, $CH^3$)

$^{31}$P-NMR (pH 6.3) δ: 9.2 s

B. Synthesis 1-(N-(5'-[phospho]-pyridoxylamino)-methylen-1,1-bisphosphonic acid:

57 mg (0.25 mmol) of ammonium salt of aminomethylenediphosphonic acid was added to the solution of 132.5 mg (0.5 mmol) of pyridoxal-5'-phosphate in 1 ml of $H_2O$ with 0.3 ml of triethylamine. The solution was stirred at room temperature for two hours. Then 20 mg (0.5 mmol) of $NaBH_4$ was added and the reaction mixture was stirred for one hour at room temperature, then neutralized up to pH 7.0 with 2N HCl. The mixture was loaded on the column with DEAE-cellulose ($HCO_3^-$); the column was washed with water and then the product of the reaction was eluted in the gradient of $NH_4HCO_3$ (0.05-0.2 M). Fractions, containing the product were evaporated with water and loaded on the column with Dowex-50 ($H^+$), the column was washed with water and then the product was eluted. To the aqueous solution of the corresponding acid aqueous ammonia solution (2.5%) was added, then the mixture was evaporated to a small volume and loaded on the column with Dowex-50 ($Na^+$), the column was washed with water and Na-salt of the product was eluted and lyophilized. The yield was 46.5 mg, 40%.

TLC: $R_f$ 0.08 on PEI-cellulose in 0.5M $NH_4HCO_3$; $R_f$ 0.2 on silufol UV 254 in isopropanol-ammonia-$H_2O$ (3:1:2).

$^1$H-NMR ($D_2O$) δ: 7.53 s (1H, 6-H); 4.78 d (2H, $J_{H,P}$ 6.9, 5-$CH_2$); 4.63 s (2H, 4-$CH_2$); 3.12 dd (1H, $J_{H,P}$ 16.5, N—CH); 2.28 s (3H, Me). $^{31}$P-NMR: 2.25 t (1P, $J_{P,H}$ 6.9, P—O); 9.15 d (2P, $J_{P,H}$ 16.5, P—C) (without proton decoupling).

The synthesis of preferred bisphosphonate conjugates with nucleotides and their analogs was carried out according to the scheme shown in FIG. 2.

Example 5

Synthesis of 5'-Fluoro-1-(2'-hydroxyethoxymethyl) uracil

The said compound was prepared according to M. Ya. Karpeisky et al, Khim. Heterocycl. Soedinenii (USSR) 1980, 11, 1541-1544.

Example 6

Synthesis of $N^4$-benzoyl-1-(2',3'-di-O-acetyl-β-D-arabinofuranosyl)cytosine

The compound was obtained analogously starting from $N^4$-benzoyl-β-D-arabinofuranosyl)cytosine (10 mmol) Yield 2.8 g (65%).

$^1$H NMR (400.13 MHz) ($CDCl_3$) δ: 8.31 d (1H, $J_{6,5}$=7.5 Hz, H-6); 7.93-7.48 m (5H, Bz), 7.76 d (1H, H-5); 6.37 d (1H, $J_{1',2'}$ 4.3 Hz, H-1'), 5.63 dd (1H, $J_{2',3'}$=2.7 Hz, H-2'), 5.24 dd (1H, $J_{3',4'}$=4.1 Hz, H-3'), 4.12 ddd (1H, H-4'), 4.01 dd (1H, $J_{5'a,4'}$=3.6 Hz, $J_{5'a,5'}$=12.3 Hz, H-5'a), 3.92 dd (1H, $J_{5'b,4'}$=4.7 Hz, H-5'b) 2.12 s (3H, Ac), 1.98 s (3H, Ac)

Example 7

Synthesis of 5-Fluorouridine 5'-monophosphate

The mixture of 2',3-di-O-acetyl-5-fluorouridine (5 mmol) and 10 ml 1 M solution β-cyanoethyl phosphate in pyridine was evaporated in vacuo and dried by coevaporations with dry pyridine (2×10 ml). The residue was dissolved in 20 ml of the same solvent, N,N-dicyclohexylcarbodiimide (DCC, 40 mmol) was added and the mixture was stored at 200° C. for 4 days. After addition of water (15 ml) the precipitating dicyclohexyl urea was filtered off and washed with 50 ml of 20% aqueous pyridine. The combined filtrates were washed with ether (2×30 ml) and concentrated in vacuo to remove the traces of ether, and then applied to a column of DEAE-cellulose (200 ml, $HCO_3^-$ form). The column was washed with water (500 ml) and eluted with 0.05 M solution of $NH_4HCO_3$. Fractions absorbing in the UV were combined, evaporated in vacuo, coevaporated with water (5×10 ml). The residue was dissolved in 40 ml of 1N NaOH and kept 20 min at 20° C. The solution was applied onto a column of Dowex 50 ($H^+$-form) and eluted with water, the resulting solution of monophosphate was neutralized by addition of 2.5% ammonia and evaporated in vacuo. The residue was dissolved in 50 ml of water and applied to a column of DEAE-cellulose (200 ml, $HCO_3^-$ form). The column was washed with water (500 ml), 0.05 M of $NH_4HCO_3$ and eluted with 0.1 M solution of $NH_4HCO_3$. Fractions absorbing in the UV were combined, evaporated in vacuo, coevaporated with water (5×10 ml). The residue was dissolved in 40 ml of water and freeze dried. 5-Fluorouridine-5'-monophosphate was obtained as ammonium salt. Yield 2.4 mmol (48%).

$^1$H-NMR (400.13 MHz) ($D_2O$) δ: 8.16 d (1H, $J_{6,F}$ 6.5 Hz, H-6), 5.92 dd (1H, $J_{1',2'}$=4.9 Hz, $J_{1',F}$=1.4 Hz, H-1') 4.32 t (1H, $J_{3',2'}$=5.0 Hz, $J_{3',4'}$=5.1 Hz, H-3'), 4.29 t (1H, H-2') 4.22 m (1H, H-4'), 4.06 ddd (1H; $J_{4',5'a-b}$=3.8 Hz, $J_{5'a,5'b}$=11.8 Hz, $J_{5'a-P}$=2.8 Hz, H-5'a), 3.98 ddd (1H, $J_{5'b,5'a}$=5.1 Hz, $J_{5'b-P}$=2.9 Hz, H-5'b).

Example 8

Synthesis of 5-Fluoro-1-(2'-hydroxyethoxymethyl)-uracil-2'-monophosphate

The mixture of 5-fluoro-1-(2'-hydroxyethoxymethyl) uracil (4.6 mmol) and 9.2 ml 1 M solution of β-cyanoethyl phosphate in pyridine was evaporated in vacuo and dried by coevaporations with dry pyridine (2×10 ml). The residue was dissolved in 20 ml of the same solvent, DCC (37 mmol) was added and the mixture was stored at 20° C. for 4 days. After addition of water (15 ml), the precipitating dicyclohexyl urea was filtered off and washed with 50 ml of 20% aqueous pyridine. The combined filtrates were washed with ether (2×30 ml) and concentrated in vacuo to remove the traces of ether and then applied to a column of DEAE-cellulose (200 ml, $HCO_3^-$ form). The column was washed with water (500 ml) and eluted with 0.05 M solution of $NH_4HCO_3$. Fractions absorbing in the UV were combined, evaporated in vacuo, coevaporated with water (5×10 ml). The residue was dissolved in 40 ml of 1N NaOH and kept for 20 min at 20° C. The solution was applied onto a column of Dowex 50 ($H^+$ form) and eluted with water, the resulting solution of monophosphate was neutralized by addition of 2.5% ammonia, evaporated in vacuo. The residue was dissolved in 50 ml of water and applied to a column of DEAE-cellulose (200 ml, $HCO_3^-$ form). The column was washed with water (500 ml) 0.05 M of $NH_4HCO_3$ and eluted with 0.1 M solution of $NH_4 HCO_3$. Fractions absorbing in the UV were combined, evaporated in vacuo, coevaporated with water (5×10 ml). The residue was dissolved in 40 ml of water and freeze dried. 5-Fluoro-1-(2'-hydroxyethoxymethyl)uracil-2'-monophosphate was obtained as ammonium salt. Yield 2.07 mmol (45%).

$^1$H-NMR (400.13 MHz) ($D_2O$) δ: 7.98 d (1H, $J_{6,F}$=5.7 Hz, H-6), 5.19 s (2H, $CH_2N$), 3.91 m (2H, $CH_2$), 3.75 m (2H, $OCH_2$)

Example 9

Synthesis of 1-(β-D-Arabinofuranosyl)cytosine-5'-monophosphate

The mixture of $N^4$-bensoyl-1-(2',3'-di-O-acetyl-β-D-arabinofuranosyl)cytosine (2 mmol) and 4 ml 1 M solution of β-cyanoethyl phosphate in pyridine was evaporated in vacuo and dried by coevaporations with dry pyridine (2×10 ml). The residue was dissolved in 5 ml of the same solvent, DCC (16 mmol) was added and the mixture was stored at 20° C. for 4 days. After addition of water (15 ml), the precipitating dicyclohexyl urea was filtered off and washed with 50 ml of 20% aqueous pyridine. The combined filtrates were washed with ether (2×20 ml) and concentrated in vacuo to remove the traces of ether, and then applied to a column of DEAE cellulose (200 ml, $HCO_3$ form). The column was washed with water (500 ml) and eluted with 0.05M solution of $NH_4HCO_3$. Fractions absorbing in the UV were combined, evaporated in vacuo, coevaporated with water (5×10 ml). The residue was dissolved in 25 ml of 1N NaOH and kept for 20 min. at 20° C. The solution was applied onto a column of Dowex-50 ($H^+$ form) (40 ml) and eluted with mixture pyridine-water 1:4 (100 ml), the resulting solution evaporated in vacuo, coevaporated with water (2×10 ml) and methanol (2×20 ml). The residue was dissolved in 5 ml 5M $NH_3$ in methanol and kept at 20° C. for 4 days. The reaction mixture was dissolved in 50 ml of water, washed with chloroform (2×20 ml) and concentrated in vacuo to remove the traces of chloroform and then applied to a column of DEAE-cellulose (200 ml, $HCO_3^-$ form). The column was washed with water (500 ml), 0.05 M $NH_4HCO_3$ and eluted with 0.1 M $NH_4HCO_3$. Fractions absorbing in the UV were combined, evaporated in vacuo, coevaporated with water (5×10 ml). The residue was dissolved in 40 ml of water and freeze dried. Yield 0.82 mmol (41%).

$^1$H NMR (400.13 MHz) ($D_2O$) δ: 7.93 d (1H, $J_{6,5}$=7.7 Hz, H-6), 6.22 d (IH', $J_{1',2'}$=5.3 Hz, H-1'), 6.08 d (1H, H-5), 4.43 t (1H, $J_{2',3'}$=51 Hz, H-2), 4.20 t (1H, $J_{3',4'}$=5.2 Hz, H-3'), 4.15 m (1H, H-4'), 4.09 m (2H, H-5'a, 5'b)

Example 10

Synthesis of bisphosphonate-nucleotide conjugates

General
NMR spectra were recorded on a Bruker AMX 400 spectrometer at 300K in $D_2O$. The chemical shifts were related to the water signal at 4.6 ppm. The signals were assigned by the aid of phosphorus decoupling measurements. The TLC-chromatography was performed on Kieselgel 60 $F_{254}$ plates developed in 2-propanol/$NH_3$ (aq., conc.)/water 7:1:2 (system A); water/$NH_3$ (aq., conc.)/trichloracetic acid/methanol 6:3:1:10 (system B) or on PEI-cellulose plates in 0.25 M $NH_4HCO_3$ (system C); 1M LiCl (system D); 0.15 M $KH_2PO_4$ (system E); 0.5 M $NH_4HCO_3$ (system F). HPLC-analysis: Column Nucleosil C-18 (30-C18), 0-4% triethylammonium acetate (0.1M, pH6.8); 20 min, flow rate 1 ml/min.

Conjugate Synthesis

To the solution of 0.2 mmol nucleotide tri-n-butylammonium salt in DMF (3 ml) 1,1' carbonyldumidazole (98 mg, 0.6 mmol) was added. The reaction mixture was stirred 1 h at room temperature, then 0.8 ml of 1M solution of methanol in DMF was added, followed after 20 min. by a solution of tri-n-butylammonium salt of diphosphonic acid (1 mmol) in DMF. The reaction mixture was stirred at room temperature 16 hours, the crystalline material formed was filtered off, washed with DMF, and the solution was evaporated in vacuo to dryness.

Isolation and Purification

Method A (Compounds I-III, FIG. 2)

The residue after evaporating to dryness was dissolved in 20 ml water and purified on DEAE-cellulose ($HCO_3^-$). The column was washed with water (500 ml) and then eluted with a linear gradient $NH_4HCO_3$ (0.05M-0.3M). Conjugates were eluted in 0.21 M $NH_4HCO_3$. The peak eluate was evaporated, the residue coevaporated with water. Lyophilization of the aqueous solution afforded ammonium salt of conjugates.

Method B (Compounds IV-IX, FIG. 2)

After evaporating, the residue was dissolved in 20 ml 0.02 M AcOLi in 0.02 M AcOH and purified on DEAE-cellulose ($AcO^-$ form). The column was washed with 0.02M AcOLi in 0.02M AcOH (200 ml), 0.04M AcOLi in 0.04M AcOH (300 ml). Analog of triphosphate was eluted in 0.2M AcOLi in 0.2M AcOH. The peak eluate was evaporated, the residue was centrifuged with ethanol (4×100 ml), dissolved in water. Lyophilisation of the water solution afforded Li salt of a triphosphate analog. In the case of the analogs (VI) and (VII) residue after lyophilisation was dissolved in 20 ml 0.5% solution triethylamine in water, the solution was kept at room temperature 30 min and lyophilized. Residue was dissolved in 2 ml water and applied to a Dowex-50 ($Na^+$) column. Sodium salt of triphosphate analogs were eluted with water and lyophilized.

Conjugates Obtained

Anhydride of 1-(2'-hydroxyethoxymethyl)-5-fluorouracil-2'-phosphate and methylenediphosphonic acid, $NH_4$-salt, method A, (II, FIG. 2)

Yield 58 mg, 55%.

$R_f$ 0.05 (A); $R_f$ 0.1 (C); $R_f$ 0.32 (D); $R_f$ 0.34 (E).

$^1$H NMR ($D_2O$) δ: 7.89 d (1H, $J_{6H,F}$=5.5; 6-H); 5.25 s (2H, N—$CH_2$); 4.0 m (2H,$CH_2$); 3.78 m (2H, $CH_2$); 2.22 t (2H, J=20.0; P—$CH_2$—P).

$^{31}$P NMR ($D_2O$) δ: −10.0 (1P, $Jp_\alpha, p_\beta$=_23.0; Pα); 11.8 m (1P, Pβ; 14.2 m (1P, Pγ).

Anhydride of 5-fluorouridine-5'-monophosphoric acid and methylenediphosphonic acid $NH_4$-salt, method A (III, FIG. 2).

Yield 75 mg, 65%. $R_f$ 0.05 (A); $R_f$ 0.11 (C); $R_f$ 0.23 (D); $R_f$ 0.4 (E).

$^1$H NMR($D_2O$) δ: 8.02 d (1H, $J_{6H,F}$=6.4; 6-H); 5.89 d (1H, $J_{1',2'}$=3.2; 1'-H); 4.29 m (2H, 2'-H, 3'-H); 4.2 m (3H, 5'-$CH_2$, 4'-H); 2.24 t (2H, J=19.9; P—$CH_2$—P).

$^{31}$P NMR($D_2O$) δ: −10.0 d (1P, $Jp_\alpha, p_\beta$=_23.0; $P_\beta$); 11.8 m (1P, $P_\beta$); 14.3 m (1P, $P_{\gamma\_}$)

Anhydride of inosine-5'-monodihosphoric acid and 1-hydroxyethylidene-1,1-disphosphonic acid, Li-salt, method B, (IV, FIG. 2).

Yield 95 mg, 84%.

$R_f$ 0.04 (B); $R_f$ 0.05 (C); $R_f$ 0.3 (D); $R_f$ 0.16 (E). HPLC: 99.5%; RT 8.98 min. (Li-salt).

$^1$H NMR ($D_2O$) δ: 8.47 s (1H, 8-H); 8.2 s (1H, 2-H); 6.2 br.s (1H, 1'-H); 4.6 m (2H, 2',3'-H; 4.41 m (1H, 4'-H); 4.28 m (2H, 5'-$CH_2$); 1.56 t (3H, J=12.0; $CH_3$).

$^{31}$P NMR ($D_2O$) δ: −9.3 m (1P, Pα); 17.0 m (1P, Pβ); 17.2 m (1P, Pγ).

Anhydride of I-(2'-hydroxyethoxymethyl)-5-fluorouracil-2'-phosphate and 1-hydroxyethylidene-1,1-disphosphonic acid, Li-salt, method B, (V, FIG. 2)

Yield 60 mg, 61%.

$R_f$ 0.05 (B); $R_f$ 0.09 (C); $R_f$ 0.32 (D). HPLC: 96.6%; RT 5.88 min. Na-salt.

$^1$H NMR($D_2O$) δ: 7.72 d (1H, $J_{H,F}$=5.5, 6-H); 5.18 s (2H, N-$CH_2$); 4.09 t (2H, $CH_2$); 3.79 t (2H, $CH_2$); 1.5 t (3H, $J_{H,P}$=15; $CH_3$).

$^{31}$P NMR ($D_2O$) δ: −8.8 d (1P, $J_{P\alpha P\beta}$=33.3; Pα); 16.2 dd (1P, Pβ); 16.8 d (1P, $J_{P\beta P\gamma}$=33.0; Pγ)

Anhydride of 5-fluorouridine-5'-monophosphoric acid and 1-hydroxyethylidene-1~I-disphosphonic acid Na-salt, method B, (VI, FIG. 2).

Yield 78 mg, 65%.

$R_f$ 0.21 (C); $R_f$ 0.2 (D); $R_f$ 0.31 (E). HPLC: 96.6%; RT 6.18 min. Na-salt).

$^1$H NMR ($D_2O$) δ: 7.88 d (1H, $J_{H,F}$=6.2; 6-H); 5.97 d (1H, $J_{1',2'}$=4.5; 1'-H); 3.38 m (1H, 2'-H); 4.3 m (1H, 3'-H); 4.24 m (3H, 4'-H, 5'-$CH_2$); 1.54 t (3H, $J_{H,P}$=14.9; $CH_3$).

$^{31}$P NMR ($D_2O$) δ: −9.2 d (1P, $J_{P\alpha P\beta}$=30.0; Pα); 16.4 m (2P, Pβ, Pγ).

Anhydride of uridine-5'-monophosphoric acid and 1-hydroxyethylidene-1,1 disphosphonic acid, Li-salt, method B (VII, FIG. 2).

Yield 80 mg, 75%.

$R_f$ 0.1 (C); $R_f$ 0.12 (D); $R_f$ 0.04 (E). HPLC:97.3%; RT 3.49 min., Na-salt.

$^1$H NMR ($D_2O$) δ: 7.8 d (1H, $J_{6,5}$7.8; 6-H); 5.9 d (1H, $J_{1',2'}$=3.8; 1'-H); 5.8 dd (1H, $J_{5,6}$=7.8; 5-H); 4.3 m (1H, 2'-H); 4.2 m (1H, 3'H); 4.19 m (3H, 4'-H, 5'-$CH_2$); 1.45 t (3H, $J_{P,H}$=15.0; $CH_3$).

$^{31}$P NMR ($D_2O$, pH 9.3) δ: −9.2 d (1P, $J_{P\alpha P\beta}$=32.0; Pα); 16.2 m (2P, Pβ, Pγ); ($D_2O$ pH5.3) δ: −9.2 d (1P, $J_{P\alpha P\beta}$=31.7; Pα); 2.8 dd (1P, $J_{P\beta, P\gamma}$=33.7, Pβ;) 17.8 d (1P, $J_{P\gamma, P\beta\_}$=33.7; $P_\gamma$)

Example 11

Synthesis of anhydride of Inosine-5'-monophosphoric acid and Methylenedisphosphonic acid, $NH_4^+$ salt, (I, FIG. 2)

Tri-n-butylammonium salt in dry DMF (3 ml) and 1,1'-carbonyldiimidazole (98 mg, 0.6 mmol) was added to a solution of 0.2 mmol of Inosine-5'-monophosphate. The reaction mixture was stirred 1 h at room temperature. TLC analysis in system iso-PrOH—NH$_4$OH—H$_2$O (7:1:2) showed that mononucleotide was completely converted to a corresponding imidazolide (R$_f$ 0.1→0.6). The 0.8 ml of 1 M solution of methanol in dry DMF was added, after 20 mm solution of tri-n-butylammonium salt of methylenediphosphonic acid (1 mmol) in DMF (3 ml) was added. The reaction mixture was stirred 16 h at room temperature. The crystalline material was filtered off, washed with DMF and the solution was evaporated in vacuo to dryness. The residue, after evaporating, was dissolved in 20 ml water and was applied to a column of DEAE-cellulose (100 ml, HCO$_3^-$ form). The column was washed with water (500 ml) and then eluted with a linear gradient of NH$_4$HCO$_3$ (0.05→0.3 M). The triphosphate analog was eluted in 0.21 M NH$_4$HCO$_3$. The peak eluate was evaporated and the residue was coevaporated with water (5×10 ml). Lyophilization of the water solution afforded ammonium salt of triphosphate analog. Yield 85 mg, 74%. R$_f$: 0.05 (A); 0.04 (B); 0.25 (C); 0.16 (D). HPLC (Column Nucleosil C-18 (30-C18), 0-4% triethylammonium acetate (0.1M, pH 6.8), 20 min., flow rate 1 ml/min): 100%, RT 7.2 min, Na salt)

$^1$H NMR (D$_2$O) δ: 8.45 s (1H, 8-H); 8.2 s (1H, 2-H); 6.1 d (1H, J$_{1',2'}$=5.4; 1'-H); 4.55 m (1H, 3'-H); 4.39 m (1H, 4'-H); 4.25 m (2H, 5'-CH$_2$); 2.32 t (2H, J$_{H,P}$=20; P—CH$_2$—P).

$^{31}$P NMR (D$_2$O) δ: −10.2 d (1P, J$_{P\alpha,P\beta}$=25; Pα); 9.8 br d (1P, Pβ); 15.4 d (1P, J$_{P\beta,P\gamma}$=7.0; Pγ)

Example 12

Synthesis of anhydride of 1-(2'-hydroxyethoxymethylene)-5-Fluorouracil-2'-phosphoric acid and 1-hydroxyethyliden-1,1-diphosphonic acid, Li salt (V, FIG. 2).

To the solution of 0.2 mmol 1-(2-hydroxyethoxymethylene)-5-Fluorouracil-2'-phosphonic acid tri-n-butylammonium salt in dry DMF (3 ml) 1,1'-carbonyldiimidazole (98 mg, 0.6 mmol) was added. The reaction mixture was stirred for 1 hour at room temperature. TLC analysis in system iso-PrOH—NH$_4$OH—H$_2$O (7:1:2) showed that mononucleotide was completely converted to a imidazolide (R$_f$ 0.15→0.65). Then 0.8 ml 1 M solution methanol in dry DMF was added, after 20 mm solution of tri-n-butylammonium salt of 1-hydroxyethylidene-1,1-disphosphonic acid (1 mmol) in DMF (3 ml) was added. The reaction mixture was stirred 16 h at room temperature. The crystalline material was filtered off and washed with DMF. The solution was evaporated in vacuo to dryness. The residue, after evaporating, was dissolved in 20 ml 0.02M AcOLi in 0.02M AcOH and was applied on to column of DEAE-cellulose (100 ml, AcO$^-$ form). The column was washed with 0.02 N AcOLi in 0.02M AcOH (200 ml), 0.04M AcOLi in 0.04M AcOH (300 ml). The triphosphate analog was eluted in 0.2M AcOLi in 0.2M AcOH. The peak eluate was evaporated, the residue was centrifuged with ethanol (4×100 ml) and then dissolved in water. Lyophilization of the water solution afforded Li salt of triphosphate analog. Yield 60 mg, 61%. R$_f$: 0.05 (B); 0.09 (C); 0.32 (1). HPLC (Column Nucleosil C-18 (30-C 18), 0-4% triethyl ammonium acetate (0.1 M, pH 6.8), 20 mm, flow rate 1 ml/min): 96.6%, RT 5.88 min (Na salt)

$^1$H NMR (D$_2$O) δ: 7.72 d (J$_{H-F}$=5.5; 6H); 5.18 s (2H, N-5-CH$_2$); 3.79 t (2H, CH$_2$); 1.5 t (3H, J$_{H,P}$=15; CH$_3$)

$^{31}$P NMR (D$_2$O) δ: −8.8 d (1P, J$_{P\alpha,P\beta}$=33.3; Pα;); 16.2 dd (1P, 1P, J$_{P\beta,P\gamma}$=7.0; Pγ)

Example 13

Synthesis of anhydride of 5-Fluoro-uridine-5'-monophosphoric acid and 1-Hydroxyethylidene-1,1-diphosphonic acid, Li salt (VI, FIG. 2).

To the solution of 0.2 mmol 5-Fluoro-uridine-5'-monophosphate tri-n-butylammonium salt in dry DMF (3 ml) 1,1'-carbonyldiimidazole (98 mg, 0.6 mmol) was added. The reaction mixture was stirred 1 h at room temperature. TLC analysis in system iso-PrOH-NH$_4$OH—H$_2$O (7:1:2) showed that mononucleotide was completely converted to a imidazolide (R$_f$ 0.13→0.7). Then 0.8 ml 1M solution methanol in dry DMF was added, after 20 min solution of tri-n-butylammonium salt of 1-hydroxyethylidene-1,1-diphosphonic acid (1 mmol) in DMF (3 ml) was added. Reaction mixture was stirred 16 h at room temperature. The crystalline material was filtered off, washed with DMF, and the solution was evaporated in vacuo to dryness. The residue, after evaporating, was dissolved in 20 ml 0.02M AcOli in 0.02M AcOH and was applied on to column of DEAE-cellulose (100 ml, AcO$^-$ form). The column was washed with 0.02 M AcOLi in 0.02 M AcOH (200 ml), 0.04 M AcOLi in 0.04 M AcOH (300 ml). The triphosphate analog was eluted in 0.2 M AcOLi in 0.2M AcOH. The peak eluate was evaporated, the residue was centrifuged with ethanol (4×100 ml), dissolved in 15 ml water and freeze dried. The residue was dissolved in 20 ml of 0.5% solution of triethylamine in water and kept for 30 min. at 20° C. and freeze dried. The residue was dissolved in 2 ml water and was applied on to a column of Dowex-50 (1 ml, Na$^+$-form). Na salt of triphosphate analog was eluted with water and freeze dried. Yield 78 mg, 65%. R$_f$: 0.05 (B); 0.21 (C); 0.2 (D); 0.31 (E). HPLC (Column Nucleosil C-18 (30-C18), 0-4% triethylammonium acetate (0.1M, pH 6.8), 20 min., flow rate 1 ml/min): 96.6%, RT 6.18 min (Na salt)

$^1$H NMR (D$_2$O) δ: 7.88 d (1H, J$_{H,F}$=6.2; 6-H); 5.97 d (1H, J$_{1',2'}$=4.5; 1'-H); 3.38 m (1H, 2'-H); 4.3 m (1H, 3'-H); 4.24 m (3H, 4'-H, 5'-CH$_2$); 1.54 t (3H, J$_{H,P}$=14.9; CH$_3$).

$^{31}$P NMR (D$_2$O) δ: −9.2 d (1P, J$_{P\alpha,P\beta}$=30.0; Pα); 16.4 m (2P, P$_{\beta\_}$, P$_\gamma$).

Example 14

Stability of Novel Bisphosphonate Conjugates

A. Determination of a Conjugate-Technetium Complex Stability

The stability of complexes formed under different conditions (water, human plasma and serum) was estimated by chromatography methods. Chromatographic studies were carried out using acetonitrile-water (3:1) solvent system. Whatman 3M paper strips (8 cm×2 cm) were used for ascending chromatography. Strips were cut into 0.5 cm sections and assayed for radioactivity, and the percent binding was determined for the labeled conjugate. Pertechnetate R$_f$ value were equal to 1.0 under these conditions. The radioisotope complex was incubated in water (24 hours), fresh human plasma and serum (5 hours) at 37° C. Samples are then withdrawn from the stirred plasma or serum immediately (at time zero) after addition and then each hour. The main product (more than 97%) was represented by compound with R$_f$ 0.1 in all experiments. Pertechnetate R$_f$ value is equal to 1.0 under these conditions.

TABLE 1

Chromatographic estimation of $^{99m}$Tc - pyridoxyl-pamidronate (i) complex stability in aqueous solution at pH 7.0

| Rf\Time | 0 | 1 hour | 5 hours | 24 hours |
|---|---|---|---|---|
| 0.1 | 98.7 | 98.5 | 98.9 | 88.48 |
| 0.2 | 0.1 | 0.25 | 0.16 | 8.52 |
| 0.3 | 0.1 | 0.12 | 0.20 | 0.53 |
| 0.4 | 0.07 | 0.08 | 0.10 | 0 |
| 0.5 | 0.11 | 0.10 | 0.07 | 0.14 |
| 0.6 | 0.12 | 0.15 | 0.09 | 0.41 |
| 0.7 | 0.16 | 0.11 | 0.05 | 0.15 |
| 0.8 | 0.18 | 0.08 | 0.13 | 0 |
| 0.9 | 0.14 | 0.08 | 0.08 | 1.33 |
| 1.0 | 0.33 | 0.49 | 0.26 | 0.55 |

*The complex was prepared according to standard protocol.
**Figures in Table represent distribution of radioactivity on chromatogram as % of initial radioactivity of the probe taken at time zero.

B. Stability of Nucleotide-Bisphosphonate Conjugates

Figure 3:
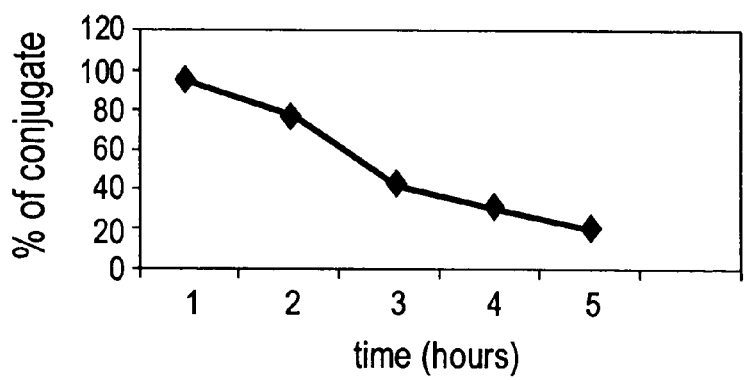
FIG. 3 demonstrates the stability of a bisphosphonate fluorouracil conjugate in human serum.

HPLC-analysis of hydrolytic stability of P(OH)(CH3)—P—O—[5~P]-5-F-Urd (conjugate VI, FIG. 2) in buffer and in human serum was carried out under the following conditions: column Nucleosil C-18 (30-C18), 0-4% triethylammonium acetate (0.1M, pH6.8); 20 min, flow rate –1 ml/min. The conjugate VI was found to be stable for several hours (more than 97%) in buffer solution at pH 5-7. Hydrolytic cleavage of the conjugate P—O—P bond occurred in course of incubation either at pH>8.0 or at pH<3.0. The stability of the conjugate was decreased in mouse/human serum as it is evidenced from data on FIG. 3. However, the conjugate is stable enough to be delivered to a skeleton in intact form.

Example 15

Binding of Novel Bisphosphonate Conjugates (NBC) on Hydroxyapatite Powder

To estimate the binding of NBC on hydroxyapatite (mineral component of a bone) UV spectra of NBC in buffer pH7 were recorded before and after treatment with hydroxyapatite. To this end 10 μl of hydroxyapatite suspension in water was added to 1 ml of ~$10^{-4}$ M solution of a NBC in 0.1 M Tris-HCl buffer, pH 7.0, 0.15 M NaCl and the mixture was intensively shaken for 10 minutes, and centrifuged for 5 minutes at 10,000 rpm in a microcentrifuge. The supernatant was separated and an absorbency spectrum of the supernatant was recorded. The corresponding values of peaks absorbency before and after hydroxyapatite treatment are given in Table 2.

TABLE 2

UV-spectra of novel bisphosphonate conjugates

| Compound | wavelength of peaks, nm | Before hydroxyapatite addition | After hydroxyapatite addition | % of nonbound compound | % of bound compound |
|---|---|---|---|---|---|
| I | 249 | 1.158 | 0.086 | 7.43 | 92.57 |
| II | 266 | 0.667 | 0.085 | 12.74 | 87.26 |
| III | 269 | 0.778 | 0.233 | 29.95 | 70.05 |
| VI | 269 | 0.567 | 0.172 | 30.34 | 69.66 |
| VIII | 272 | 0.795 | 0.09 | 11.32 | 88.68 |
| (i) | 326 | 0.391 | 0 | 0 | 100 |
| (ii) | 326 | 0.758 | 0 | 0 | 100 |
| (iii) | 326 | 0.462 | 0 | 0 | 100 |
| (iv) | 326 | 0.463 | 0 | 0 | 100 |

Example 16

Misdistributions in Rats of Vitamin B6-bisphosphonate Conjugates in Complex with $^{99m}$Tc Preparation of the Composition for a Diagnostic Test:

The probes were prepared with molar concentration of a conjugate $10^{-3}$, pH 6.5, molar ratio SnCl$_2$ to a conjugate 1:10 and 1 mCi/ml of pertechnetate.

Determination of Biodistributions in Rats

Male rats weighing 160-140 g were injected intravenously via the tail vein. The rats were sacrificed and dissected at selected times—30 min., 60 min., and 120 min. The activity uptake in bone, blood, muscle, liver and spleen of each rat was measured. The results obtained indicate 40-45% of initial radioactivity injected was accumulated at bone skeleton after 60-90 min.

TABLE 3

Ratio (%) of radioactivity accumulated in bone to that of other organ/tissue[1]

| | Bone/muscle | | | Bone/blood | | | Bone/liver + spleen | | |
|---|---|---|---|---|---|---|---|---|---|
| | 0 min | 60 min | 120 min | 0 min | 60 min | 120 min | 0 min | 60 min | 120 min |
| Medronate[2] | 5.1 | 4.2 | >80 | 20.1 | 47.5 | >380 | 6.0 | 63.3 | 112.3 |
| Formulation 1[3] | 6.4 | 94.8 | >80 | 12.2 | 316 | 456.4 | 54.7 | 220.0 | 313.7 |
| Formulation 2[4] | 8.7 | 24.2 | >80 | 16.4 | 43.4 | 216.7 | 6.5 | 132.4 | 247.6 |

[1]Each figure represents average from 3 rats
[2]Medronate - commercially available standard preparation on basis of methylenbisphosphonate
[3]Formulation 1 - preparation on basis of 3-(N-pyridoxylamino)-1-hydroxypropyliden-1,1-bisphosphonic acid
[4]Formulation 2 ¥ preparation on basis of 3-(N-[5'-phosphopo]pyridoxylamino)-1-hydroxyropyliden-1,1¥bisphosphonic acid

Example 17

Application of Compositions of Vitamin B₆-bisphosphonate Conjugates for Bone Imaging Once the complex was determined to be stable in PBS and fresh plasma, a series of gamma camera imaging studies were performed wherein imaging results are determined at time points beyond two hours, and preferably at 4 and at 6 hours. The blood pool utilized should preferably be cleared by time points beyond two hours and the bony skeleton should be obvious as in bone images using Medronate-$^{99m}$Tc images.

Two rabbits were used for experiments to compare radioactivity accumulation on normal and damaged leg. A periostium (2×0.5 cm) was removed from one of a rabbit's leg and pyridoxylpamidronate (i) preparation (1.2 ml; 5 mCi) was injected into a vein after 14 days (time needed for bone's callosity to form). Radioactivity accumulation in a damaged area was checked after 3 hours. Results (expressed in number of impulses) are given in Table 4.

TABLE 4

| Accumulation of radioactivity at rabbit leg | | |
|---|---|---|
| Organ/Rabbit | Rabbit 1 | Rabbit 2 |
| Damaged leg | 3408 | 15124 |
| Normal leg | 2048 | 3362 |
| Ratio | 1.66 | 1.52 |

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A bone targeting bisphosphonate conjugate having the structure:

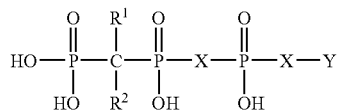

or a pharmaceutically acceptable acid addition salt thereof wherein,

X is O,

Y is an anti-cancer compound,

R¹ selected from the group consisting of OZ, NZ, SZ, OH, SH, NH₂, and NH;

R² is Z; and,

Z is selected from the group consisting of alkyl, cycloalkyl, aryl, heteroaryl, and NH₂.

2. A pharmaceutical composition comprising a compound of claim 1 and a pharmaceutically-acceptable carrier.

3. The bisphosphonate conjugate of claim 1, wherein Y is

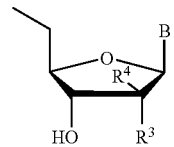

and wherein,

R³ and R⁴ are independently H, OH or F; and,

B is a natural or modified nucleic base.

4. The bisphosphonate conjugate of claim 3, wherein B is selected from the group consisting of

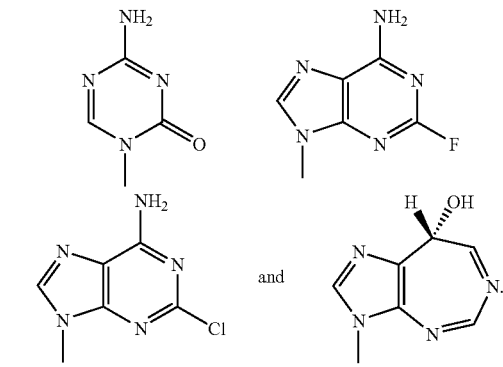

5. The bisphosphonate conjugate of claim 1, wherein Y is

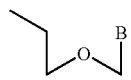

and, B is a natural or modified nucleic base.

6. The bisphosphonate conjugate of claim 5, wherein B is selected from the group consisting of

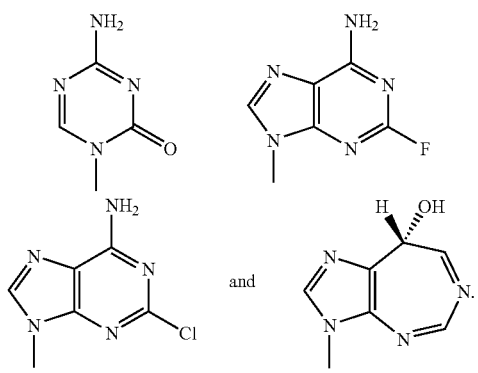

7. The bisphosphonate conjugate of claim 1, wherein Y is selected from the group of anti-cancer compounds consisting of cytarabine, doxorubicin, epirubucin, and streptozocin.

8. A bisphosphonate conjugate having the structure:

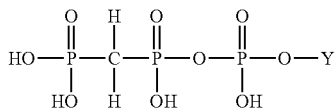

or a pharmaceutically acceptable acid addition salt thereof wherein,
Y is

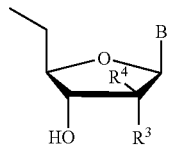

and wherein,
R³ and R⁴ are independently H, OH or F; and,
wherein B is selected from the group consisting of

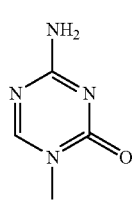 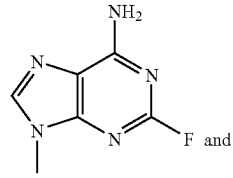

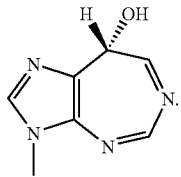

9. A pharmaceutical composition comprising a compound of claim 8 and a pharmaceutically-acceptable carrier.

10. A bisphosphonate conjugate having the structure:

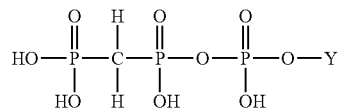

or a pharmaceutically acceptable acid addition salt thereof wherein,
Y is

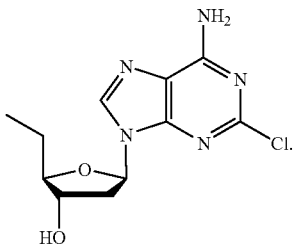

11. A pharmaceutical composition comprising the compound of claim 10 and a pharmaceutically-acceptable carrier.

12. A method of delivering an anticancer compound to the bone and/or surrounding tissue, the method comprising administering to a patient in need thereof a therapeutically effective amount of the bisphosphonate conjugate of claim 1.

13. The bisphosphonate conjugate of claim 3, where R³=R⁴=F, and B is

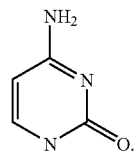

* * * * *